United States Patent
Murphy, Jr.

[11] Patent Number: 5,985,141
[45] Date of Patent: Nov. 16, 1999

[54] COOLANT RECONDITIONING SYSTEM

[76] Inventor: Edward L. Murphy, Jr., 677 Temple St., Duxbury, Mass. 02332

[21] Appl. No.: 09/249,173

[22] Filed: Feb. 12, 1999

[51] Int. Cl.⁶ .............................. B01D 24/16; F01M 9/02; B21B 45/02; A61L 2/16
[52] U.S. Cl. ......................... 210/205; 210/206; 210/168; 210/195.1; 210/196; 210/416.5; 210/501; 210/509; 210/763; 210/764; 210/749
[58] Field of Search .................................. 210/763, 764, 210/749, 509, 205, 206, 168, 416.5, 197, 501, 196, 195.1

[56] References Cited

U.S. PATENT DOCUMENTS

| | | |
|---|---|---|
| 553,383 | 1/1896 | Bailey ........................ 210/757 |
| 3,377,275 | 4/1968 | Michalski . |
| 3,518,917 | 7/1970 | Sluham . |
| 3,841,490 | 10/1974 | Hoffman . |
| 4,279,762 | 7/1981 | Lewis . |
| 4,642,192 | 2/1987 | Heskett .................... 210/638 |
| 4,772,402 | 9/1988 | Love . |
| 4,975,109 | 12/1990 | Friedman, Jr. . |
| 5,047,157 | 9/1991 | Hoffman . |
| 5,122,274 | 6/1992 | Heskett . |
| 5,135,654 | 8/1992 | Heskett .................... 210/638 |
| 5,198,118 | 3/1993 | Heskett . |
| 5,373,615 | 12/1994 | Webb ....................... 29/163.8 |
| 5,443,735 | 8/1995 | Kirnbauer ................. 210/668 |
| 5,445,945 | 8/1995 | Drechsler . |
| 5,599,454 | 2/1997 | Heskett . |
| 5,599,457 | 2/1997 | Fanning et al. . |
| 5,772,871 | 6/1998 | Lyon . |

*Primary Examiner*—Thomas M. Lithgow
*Attorney, Agent, or Firm*—John P. McGonagle

[57] ABSTRACT

A two part system providing initial filtration of free oil and dirt followed by biological filtration with a copper wool and brass wool filter medium.

10 Claims, 2 Drawing Sheets

COOLANT RECONDITIONING SYSTEM

BACKGROUND OF THE INVENTION

This invention relates to filter systems, and in particular to a filter system particularly useful for reconditioning water-soluble coolants.

Metalworking oils are used in industries as diverse as machine shops and machinery manufacturing. Water-based cooling and lubricating oils are routinely sprayed into metal-cutting and shaping equipment. Because the oils, especially in water-soluble coolant form, are generally recaptured and recycled, they often end up containing a mixture of bacteria and other contaminates that increase machine operator health risks and corrode machinery. Because machines often spray coolants into the ambient area both in droplet form and vapors, all parts of the machinery are adversely affected. Also, it is common for machine operators to experience chronic dermatitis and lung problems from biological growth in water-soluble machine coolants. Historically, machine operators have tried to protect themselves with gloves and masks. Generally, this has not been practical. Another solution has been to add chemical agents formulated to kill bacteria to the coolant. However, bactericides are themselves harsh and toxic, presenting other dangers to machine operators. To protect machinery and machine operators, coolants must be frequently changed. This raises other problems involving disposal of bacteria-contaminated coolant as well as cost to frequently replace coolant.

Economically speaking, the most important metal-corroding and coolant-destroying microbe are the anaerobic, sulfate-reducing bacteria. These bacteria produce hydrogen sulfides, which react with iron, corrode metals and destroy coolants.

SUMMARY OF THE INVENTION

The present invention provides a filtration system which removes particulate matter and free oil, and then eliminates bacteria in water-soluble coolants. The invention is particularly effective in removing anaerobic bacteria, thereby protecting machinery and machine operators as well as extending the life of the coolant with a resulting savings in time and money. The filtration system is a two part system providing initial filtration of free oil and dirt followed by a contact chamber with a brass and copper wool packed element. Applicant has found that substantially all bacteria in the filtered water-soluble coolant is eliminated. The use of brass wool and copper wool eliminates the toxicity of bactericides, copper leachate and chlorine solutions. The coolant may be reused without side effects, thereby eliminating disposal problems.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 1:
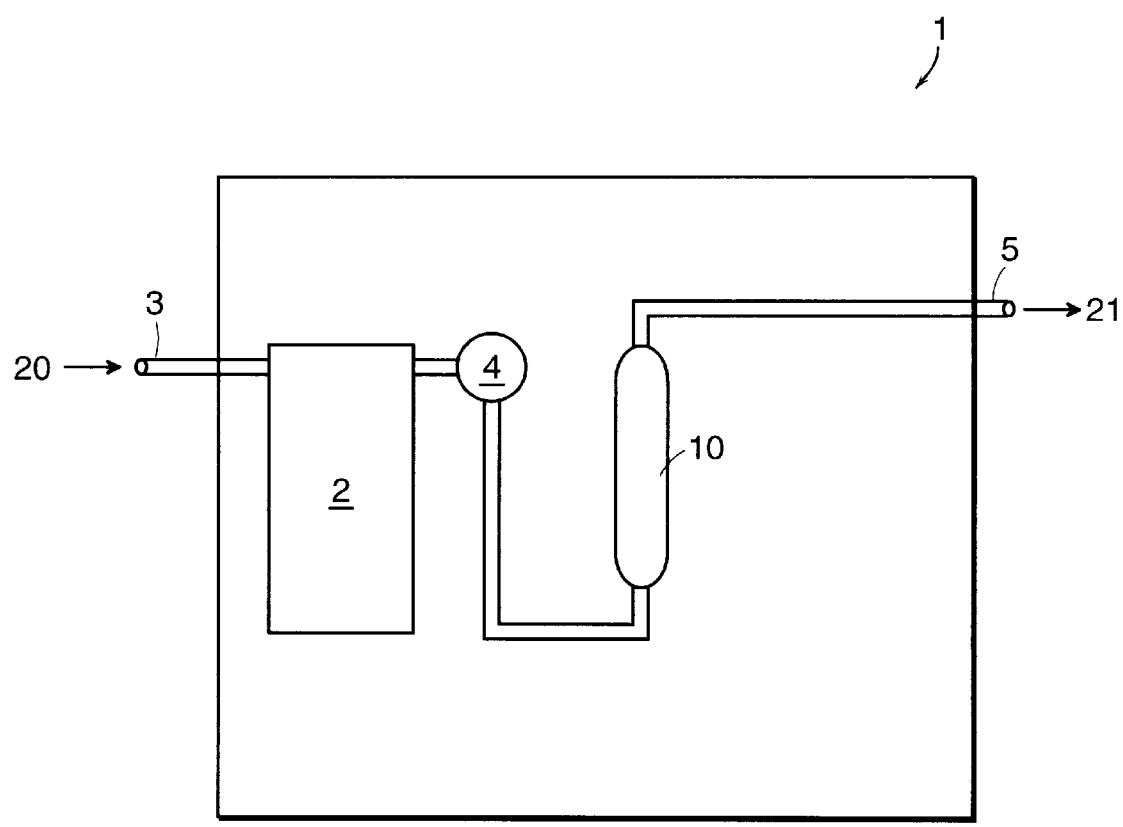
FIG. 1 is a schematic block diagram of a filter system constructed according to the present invention.

Referring to the drawings in detail wherein like elements are indicated by like numerals, there is shown an embodiment of the invention incorporating a filter system 1 constructed according to the principles of the present invention. The filter system 1 is a two part filter system comprised of a bag filter 2 for removing free oil and dirt from used, water-soluble, machine tool coolant 20 and a contact chamber 10 for controlling biological contaminants in the coolant 20. The bag filter 2 has a filter medium comprised of polypropolene, wool and cotton. The filter system 1 has a pump 4 which draws contaminated coolant 20 into an input pipe 3, through the bag filter 2, and pushes the coolant through the contact chamber 10, and out of the filter system through an output pipe 5 as bacteria-free coolant 21. See FIG. 1.

Figure 2:
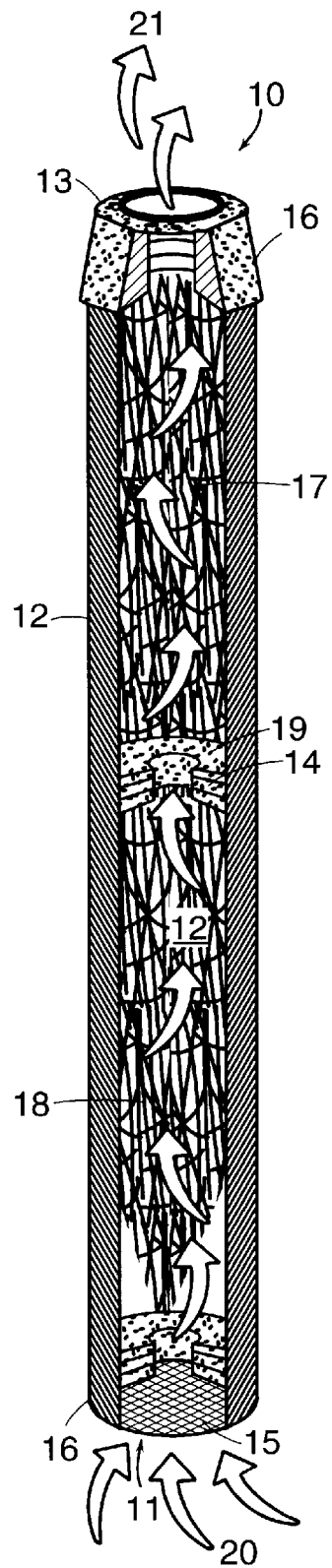
FIG. 2 is a schematic diagram of a contact chamber within the filter system.

The contact chamber 10 is comprised of a hollow, tubular element having a bottom 11 from which cylindrical side walls 12 extend vertically upward, said element 10 being generally cylindrical in shape and having a longitudinal axis generally perpendicular to the bottom 11 of said element. The element 10 has a top 13 connected to said cylindrical side walls 12, said top 13, bottom 11 and side walls 12 defining an element interior 14. The bottom 11 has a retaining screen 15 attached thereto. A gasket seal 16 is attached to the element top 13 and to the bottom 11. The element interior 14 is packed with brass wool 17 and copper wool 18. In this embodiment of the invention the brass wool 17 is positioned vertically above (downstream) the copper wool 18. A porous disk 19 is positioned within the element interior 14 in a plane transverse to the central, longitudinal, vertical axis of the element 10. The porous disk 19 prevents channelling through the element 10. See FIG. 2.

Coolant 20 to be decontaminated enters the element interior 14 from the bottom 11 passing through the retaining screen 15. The coolant 20 upflows through the copper wool 18, porous disk 19 and brass wool 17 and exits through the element top 13 as filtered and decontaminated coolant 21. The copper wool 18 is highly toxic to bacteria, killing substantially all of the bacteria in the coolant 20. The addition of brass wool 17, which is in itself is also highly toxic to bacteria, has a synergistic effect substantially increasing the killing effect on the bacteria. The brass wool also picks up any dissolved or leached copper in the coolant stream.

The brass wool 17 is a coarse grade with an average fiber width of 5 mils/0.005 inch. The copper wool 18 is also coarse grade with a purity greater than 99.9%. In this embodiment of the invention, the brass wool 17 and copper wool 18 are packed in concentrations of 0.05 ounces per cubic inch. A packing variation of ±15% appears to be equally effective. In this embodiment of the invention the filter media combination of brass wool 17 and copper wool 18 is 50% brass wool and 50% copper wool. Applicant believes that a proportion of brass wool to copper wool in the range from 25% to 75% of total filter media will also be effective.

Copper is a highly effective bactericide. The addition of copper wool to the contact chamber provides a highly effective medium for killing bacteria. However, copper in wool form bleeds or leaches a small amount into the coolant stream. Brass is known to have an affinity for heavy metals. There is an advantage to also using brass wool because of its affinity for picking up dissolved and leached copper from the coolant stream. Therefore, if any copper leaches into the coolant stream, the brass will clean it out from the coolant stream.

Brass wool has also been found by applicant to be highly effective in killing bacteria. Applicant has found that passing a coolant stream with an average bacteria coli of 100 colonies/100 ml through a filter element with only brass wool resulted in the killing of all of the bacteria colonies. The test was repeated four times with the same results. Of the different forms of brass experimented with, only brass wool appears to be 100% effective in killing bacteria. Although brass wool in itself may be a sufficient filter media to kill bacteria, applicant believes the seriousness of the dermatitis and lung infections experienced by machine operators makes it desirable to add copper wool to completely eliminate all biological contaminants in the coolant stream. However, as may be seen from Table 1 below, there is a synergistic effect to using both copper wool and brass wool, with the brass wool increasing the effectiveness of the copper wool in killing bacteria.

Applicant has found in tests that the combination of copper wool and brass wool is particularly effective in reducing anaerobic bacteria and staphylococcus. Table 1 demonstrates the effectiveness of brass wool filtration alone (B), copper wool filtration alone (C), and copper wool/brass wool combination filtration (C/B).

TABLE 1

|   | Filtration | Anaerobic/Facultative Plate Count CFU/mL | Staphylococcus/mL |
|---|---|---|---|
| 1 | W/O Filtration | 2,600,000 | 150,000 |
| 2 | B | 160,000 | 3,700 |
| 3 | C | 72,000 | 950 |
| 4 | C/B | 33,000 | 310 |

As may be seen from the table, brass wool or copper wool is effective in reducing bacteria. However, the combination of brass wool with copper wool, doubles the effectiveness of the copper wool. There is clearly a synergistic effect in using this combination. In the tests presented in Table 1, the sample used was a highly contaminated coolant that had been in use for over six months and was stored in barrels for disposal. For filtration tests, the sample was divided into four even portions. One portion was tested without filtration. The other three portions were each passed through a separate filter element, i.e., one comprised of brass wool (B), a second comprised of copper wool (C), and a third comprised of copper wool and brass wool (C/B). The filter sample portions were each recycled through their respective filter elements for 30 minutes. The results are illustrated in Table 1. The bacteria had been reduced by over 99%.

It is understood that the above-described embodiment is merely illustrative of the application. Other embodiments may be readily revised by those skilled in the art which will embody the principles of the invention and fall within the spirit and scope hereof.

I claim:

1. A filter system for reconditioning water-soluble, machine tool coolant having free oil, dirt, and biological contaminants, comprising:

a bag filter for removing free oil and dirt from said coolant; and a contact chamber for controlling biological contaminants in the coolant, said chamber being packed with a filter media comprised of brass wool and copper wool.

2. A filter system as recited in claim 1, wherein:

the contact chamber is comprised of a hollow, tubular element having a bottom from which cylindrical side walls extend vertically upward, said element being generally cylindrical in shape and having a longitudinal axis generally perpendicular to the bottom of said element, said element having a top connected to said cylindrical side walls, said top, bottom and side walls defining an element interior, said element interior being packed with brass wool and copper wool.

3. A filter system as recited in claim 2, wherein:

said brass wool is positioned vertically above and downstream of the copper wool.

4. A filter system as recited in claim 3, further comprising:

a pump positioned between and connected to the bag filter and contact chamber, said pump being adapted to draw contaminated coolant from a supply into an input pipe connected to said bag filter, through the bag filter, and being adapted to pushing the coolant through the contact chamber, and out of the filter system through an output pipe.

5. A filter system as recited in claim 4, further comprising:

a retaining screen attached to the tubular element bottom;

a porous disk positioned within the tubular element interior in a plane transverse to said central, longitudinal, vertical axis of the element;

wherein the pump pushes the coolant into the element interior through the element bottom passing through the retaining screen, said coolant upflowing through the copper wool, porous disk and brass wool and exiting through the element top as filtered and decontaminated coolant.

6. A filter system as recited in claim 5, wherein:

the proportion of brass wool to copper wool ranges from 25% to 75% of total filter media.

7. A filter system as recited in claim 6, wherein:

the brass wool and copper wool are packed in a concentration range of 0.05±15% ounces per cubic inch.

8. A filter system as recited in claim 7, wherein:

said brass wool is comprised of a coarse grade with an average fiber width of 5 mils/0.005 inch; and said copper wool is comprised of a coarse grade with a purity greater than 99.9%.

9. A filter system as recited in claim 8, further comprising:

two gasket seals, one attached to the element top and to one attached to the element bottom.

10. A filter system as recited in claim 9, wherein:

said bag filter has a filter medium comprised of polypropolene, polyester, wool and cotton.

* * * * *